United States Patent [19]

Staab et al.

[11] 4,287,764
[45] Sep. 8, 1981

[54] FLUID ANALYZER CONSTRUCTION AND HOUSING

[75] Inventors: Joachim Staab; Willy Apel, both of Frankfurt am Main; Heinz Wolf, Kronberg, all of Fed. Rep. of Germany

[73] Assignee: Hartmann & Braun Aktiengesellschaft, Frankfurt, Fed. Rep. of Germany

[21] Appl. No.: 126,730

[22] Filed: Mar. 3, 1980

[30] Foreign Application Priority Data

Mar. 2, 1979 [DE] Fed. Rep. of Germany ....... 2908169

[51] Int. Cl.³ .................. G01D 11/24; H05K 5/00; G01R 1/04
[52] U.S. Cl. .................... 73/431; 361/391; 361/415
[58] Field of Search ............ 73/431, 23, 53; 361/380, 391, 393, 394, 395, 415

[56] References Cited

U.S. PATENT DOCUMENTS

| | | | |
|---|---|---|---|
| 2,903,626 | 9/1959 | Nye et al. | 361/395 |
| 3,276,241 | 10/1966 | Hubner | 73/23 |
| 3,842,679 | 10/1974 | Iwao et al. | 73/431 X |

FOREIGN PATENT DOCUMENTS 1398601  3/1965  France ................. 361/395

*Primary Examiner*—James J. Gill
*Attorney, Agent, or Firm*—Smyth, Pavitt, Siegemund & Martella

[57] ABSTRACT

Two similarly dimensioned cases are preferably placed one on top of the other, with air space and electrical connections between them. The upper case has a door with a window and contains a slide-out and swing-out frame holding the indicating instrument and PC boards. The power supply is on the rear wall. The lower case has a slide-out tray, a door is hinged on the front edge, and on a horizontal axis. The tray supports the analyzer proper with incorporated preamplifiers. Both doors have sealing strips on the inside and can be bolted.

10 Claims, 2 Drawing Figures

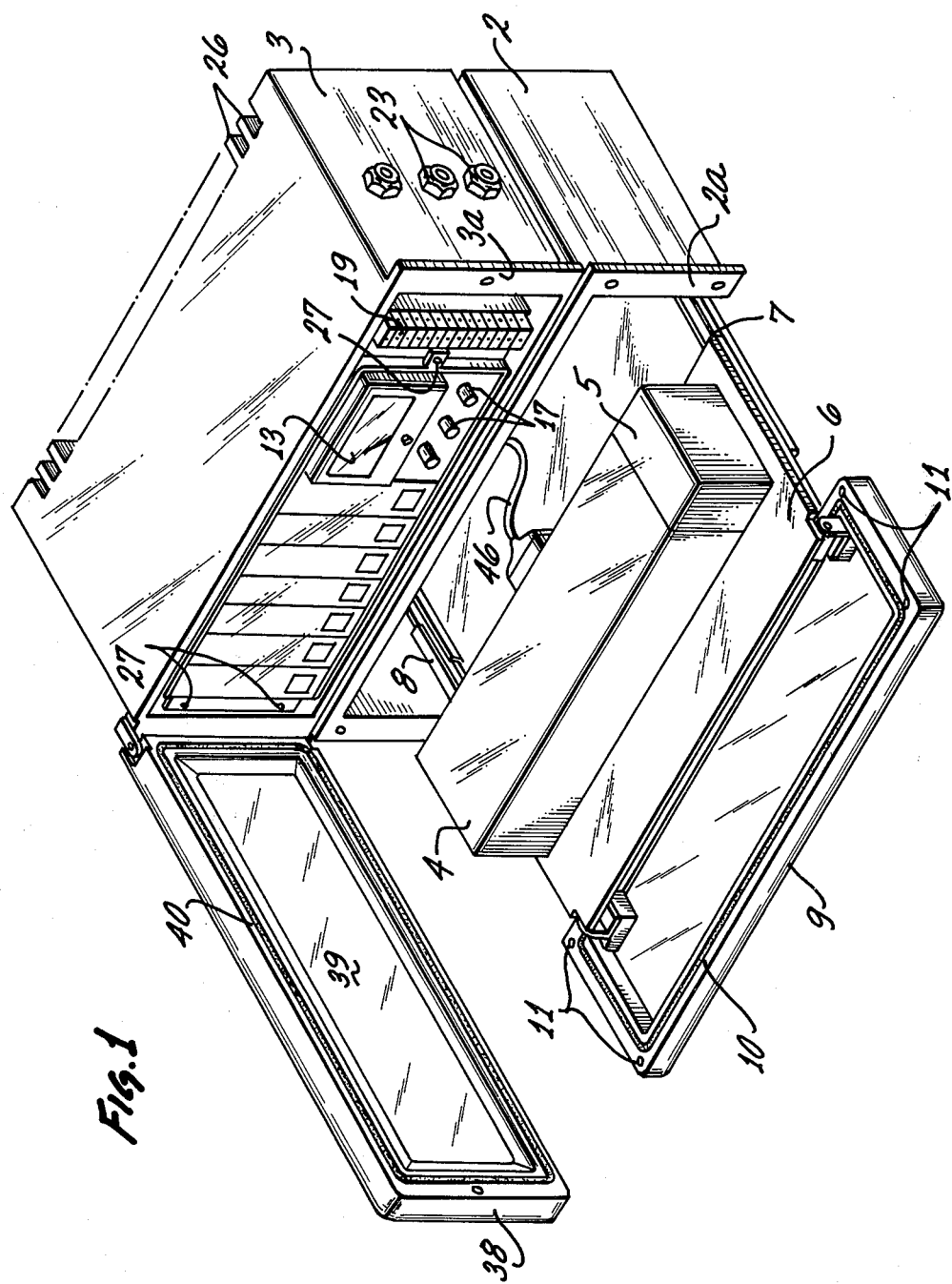

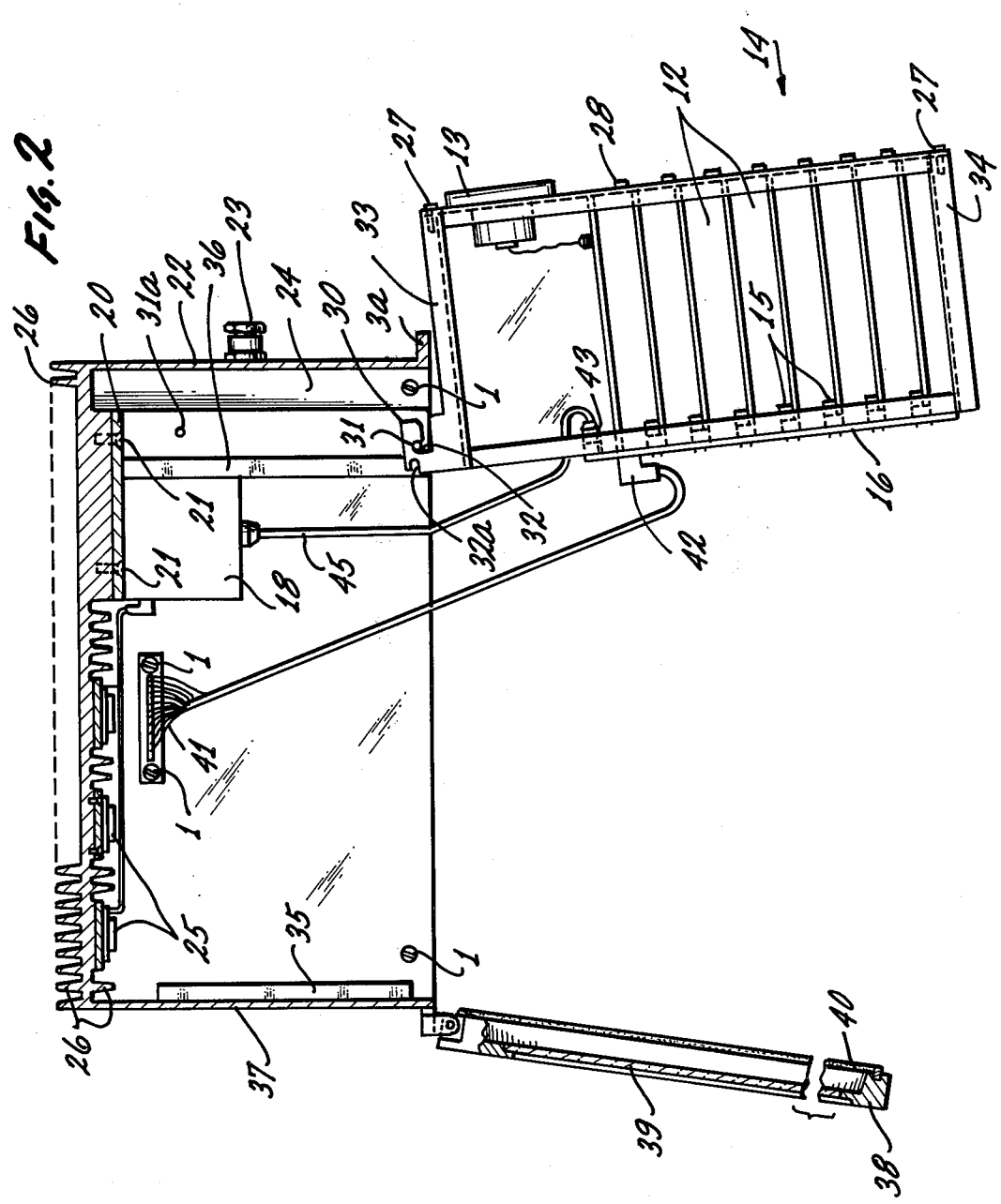

FLUID ANALYZER CONSTRUCTION AND HOUSING

BACKGROUND OF THE INVENTION

The present invention relates to an apparatus for analyzing gases, liquids, or fluids; and more particularly, the invention relates to improvements of analyzers such as described in the operating manual for the unit traded under the designation "42 CG 58-1 en" by the assignee corporation, Hartmann & Braun Mess- Und Regeltechnik.

The known apparatus includes an analyzer with pre-amplifier mounted in a case, but being separated from the requisite power supply and other circuit elements by means of a horizontal partition; the analyzer parts are mounted on a plate which is contained in the lower compartment; this plate extends in approximately the center plane of that compartment and is mounted therein in drawer-like fashion for ease of access. The preamplifier is also mounted to that plate.

The upper compartment has a hinged front panel carrying on its inside additional electric circuit elements, while the power supply proper and connection plugs, etc., are mounted to the back of that upper compartment. A removable (vertical) cover plate separates the components mounted on the hinged front (when closed) and those mounted to the rear. The lower compartment is also normally closed by a door. The two doors can be sealed and bolted shut.

The upper door or panel derives its name from the fact that it carries also an indicating instrument. A little flap is hinged to that door, covering (protecting) manual control knobs. The unit also includes a thermostat-controlled, radial fan in order to obtain a uniform temperature for all parts of the analyzer in the lower compartment.

DESCRIPTION OF THE INVENTION

It is an object of the present invention to provide an improved mounting structure and enclosure for analyzers of the type referred to above; the improvements relate in particular to maintenance and ease of operation.

It is a particular object of the present invention to improve the mounting and assembly of a gas or liquid analyzer proper with an incorporated preamplifier; a power supply means; an indicating instrument; and electric circuit elements operatively inteconnecting the power supply, the analyzer, and the indicating instrument.

In accordance with the preferred embodiment of the present invention, it is suggested to provide two preferably similarly dimensioned cases. One case holds just the analyzing equipment proper with incorporated preamplifier and being mounted on a slide-out carrier or tray on whose front edge the door for that case is hingedly mounted for hinging on a horizontal axis. The other case has a hinged door, preferably with a window, and contains a slide-out and hinged, swing-out frame for PC boards and the instrument. This other case contains also the power supply unit with a terminal block which preferably serves also as hinge support as well as for supporting one side of the frame as to sliding in and out. Additional slide rails are provided on the opposite wall of this case.

The two cases can be placed separately, or one on top of the other, but with air space in between for thermal isolation. At least some walls of the cases are provided with cooling ribs, and the power supply is preferably mounted on its own heat sink.

DESCRIPTION OF THE DRAWINGS

FIG. 1 is a perspective view from the front and the top of a two-case analyzer housed in accordance with the preferrred embodiment of the invention, showing an open door and certain parts pulled out; and FIG. 2 is a cross-section of the equipment shown in FIG. 1, the section plane being taken directly underneath the top of the upper case.

Proceeding now to the detailed description of the drawings, the figures show a case construction for a fluid analyzer which construction is comprised of a lower case 2 and an upper case 3 of box-like constructions (parallelepiped). Each case or box has a wide top and corresponding bottom, side walls (such as wall 37 of case 3) and a rear wall, but is open at the front. The two cases are of similar dimensions and interconnected by screws or bolts 1. Spacer pieces and sealing elements at the bolted connector are preferably interposed between the top of case 2 and the bottom of case 3, the spacers leave an air space in between.

The analyzer proper, designated by numeral 4, is contained in lower case 2; a preamplifier 5 for the analyzer is structurally combined therewith as an incorporated end element. All of the other circuit elements and components are contained in the upper case, 3. A plug-in type connection 46 leads from a suitable terminal of analyzer 4 to a terminal connector (not shown) in the top of lower case 2. That terminal connector may plug in directly in a terminal connector 41 in the bottom of the uper case, 3. This terminal connector 41 is visible in FIG. 2 as that figure shows a view onto that bottom. The plugs or connectors, such as 41 and as provided in both cases, are gas-tightly sealed in the bottom and top of, respectively, cases 3 and 2.

The analyzer 4 with preamplifier 5 is mounted on a carrier plate 6 or pull-out tray which, in turn, is held on a telescopic rail construction 7 and 8, to be pulled out of, or pushed into, the case or compartment 2. The plate, as so mounted, is restricted to a limit position for preventing complete pull-out; convenient stops (not shown) are provided for the purpose.

A front door 9 for the lower compartment of case 2 is hinged to the front edge of plate 6, for pivoting on a horizontal axis and to be folded down into the position shown in FIG. 1. The door, 9, thus becomes generally horizontally aligned with the support structure for carrier plate 6. This front door, as so folded down, can be used as a tray on an auxiliary table during maintenance operations. Particularly in stations in which such a device and unit is permanently installed, the folded-down door serves as a convenient work table, or the like.

Door 9 can be folded up, and upon pushing plate 6 into case 2, the inside edge portion of the door will abut flanges, such as 2, around the front opening of the case, whereby particularly threaded bores 11 are aligned in pairs. Bolts can be inserted to tighten the door to the case. A sealing strip 10 along the inside edge surface of the door seals the interior of the case when the door is bolted down by easy to remove screws.

As stated, the other components of the device are contained in upper case 3. A frame 14 is hinged generally in or inside the upper case 3, and printed circuit boards 12 are inserted side by side in that frame. The boards 12 hold the several electrical circuit components and elements needed to run the analyzer, including those elements which receive a signal from amplifier 5 in the lower case. Also, the analyzer requires that several control and regulating functions be carried, and the requisite circuit elements are mounted on these PC boards 12.

The frame 14 holds also an indicating, measuring instrument and a panel for adjusting and operating knobs 17. These knobs are provided for adjusting the sensitivity of the device and for different ranges. Also, function test switches may be included in this operation panel.

The instrument and the operating knobs of unit 13 are connected to one of the PC boards 12. These boards carry terminal connectors 15 (pins) along their rear, to be plugged into terminal sockets on a master PC board 16. This board 16, in turn, is connected to a flexible cable 44 by means of a plug connection 42, the other end of this multilead cable is connected to a plug 41 to be plugged into the companion plug of the lower case as described above, to complete the connection via cable 46 (FIG. 1) to the analyzer 4.

The portion of frame 14 in the rear of instrument 13 is unoccupied as far as frame-mounting is concerned, but permits insertion of a power unit 18, when frame 14 is fully inserted in case 3. This unit 18 is a compact module which includes a transformer for connection to the mains, a line switch, a rectifier, and smoothing filters in order to provide a substantially ripple-free dc voltage at the desired level. These units or modules are conventional and not shown in detail; they are available in a compact, box-like encasing and construction. The power supply unit 18 is mounted on a plate 20, serving as heat sink and being bolted to the rear wall of case 3 by means of screws 21.

A terminal block 19, accessable from the front is also mounted on the heat sink plate by means of screws 21. The terminal block is provided for connection to a cable that runs through feed-through bores 23, or the like. A space 24 is particularly provided between a sidewall 22 of case 3, having these through-connections 23, and the terminal block 19 to accommodate cable leads running from connections 23 to the connectors of terminal block 19. Further connections from the latter are then made to the power supply unit 18.

Power amplifier elements 25 are bolted to the rear wall of case 3. These elements require cooling. Accordingly, the rear wall as a whole serves as a heat sink and is particularly provided with cooling ribs 26, on the inside as well as on the outside. Similar cooling ribs are provided on the rear wall of lower case 2 and on the inside of the tops of both cases. These ribs facilitate removal of heat which develops in various parts, such as the power amplifiers, the supply part, the analyzer, etc. It is important in this regard that an air gap exists betwen the two cases, 2 and 3, established by spacers but permitting air to flow through. The two cases are thus thermally isolated from each other.

As far as frame 14 and its mounting is concerned, it is provided along its upper portion with rearwardly extending rails 33 and 34 which can also be termed overhung edges. The frame can be suspended inside case 3, by hanging engagement with rails 35 and 36; rail 35 extends from a side wall 37 of the case, and rail 36 extends from block 19. The frame 14 can thus be slid in and out of the case.

In addition, rail 33 has an extension 30 with two slots. One slot, 32, is angled and receives a pin 31. This way, frame 14 is pivotably mounted and hinged. Pin 31 extends up from block 19. Another pin 31a, extends also up, more to the rear. When frame 14 is swung in and shifted into case 3, pin 31a will be inserted into the second slot 32a of piece 30, serving as a stop.

Of course, as soon as frame 14 is slid back, pin 31 will slide out of slot 32; inserted frame 14 can additionally be screwed to the case and the terminal block by means of screws or bolts 27. Conversely, when frame 14 is pulled out, pin 31 will enter slot 32 when the frame is just about out, and that will limit pull-out of the frame and establish the hinged connection. The frame can now be swung out, as shown in FIG. 2. Through further manipulation of slot 32, one may remove the frame entirely.

There is a similar arrangement of rail and a hinge in the lower surface of the frame, the hinges particularly includes a pin which extends down from the lower surface of block 19.

The upper case 3 has a front door 38, along whose inner edge runs a sealing strip 40. The center portion 39 of that door is a window for observing instrument 13. When the door is closed, bolts can be inserted for bolting the door to flanges 3a.

The lower case 2 requires, in addition, tubular inlets and conduits for feeding fluid to and through analyzer 4. These conduits have been omitted from the sake of clarity; they run gas tightly and sealed through the rear wall, the bottom, and/or a side wall of case 2.

One can readily see that the two cases 2 and 3 can be completely separated and placed in separate locations. One needs a cable connection between plug 41 of case 3 and the corresponding plug in the top of case 2.

The invention is not limited to the embodiments described above; but all changes and modifications thereof, not constituting departures from the spirit and scope of the invention, are intended to be included.

We claim:

1. In an analyzer arrangement for gas or liquid which includes an analyzer means, an indicating instrument, power supply means, and electric circuit elements, a combination for mounting and assembly, comprising:

a first case and a second case, each having a front being open for access;

the first case including or containing (a) a carrier plate or tray mounted for insertion and retraction; (b) a door hinged to a front edge of the carrier plate about a horizontal axis, for sealingly closing the open front of the first case and bolting thereto when the plate is inserted in the first case, the door being capable of folding down into a horizontal position when the plate is pulled out, the analyzer means with preamplifier mounted on the plate to be contained in the first case when the plate is inserted;

the second case containing (a) the power supply means mounted inside the second case; (b) a frame in the second case for holding the instrument and a plurality of printed circuit boards for said circuit elements; (c) means for slideably and hingedly positioning the frame in the second case to permit full access of a rear of the frame; and (d) a door hinged to the second case for sealingly closing and bolting to the second case; and electrical connection means including a removable or disconnectable portion for connecting the analyzing means in the first case to circuit elements on the boards in the second case.

2. The combination as in claim 1, there being means for mounting one of the cases on top of the respective other one, leaving air space in between for the purpose of thermally isolating the cases from each other.

3. The combination as in claim 1, said power supply unit being mounted to a heat sink plate which, in turn, is mounted to a rear wall of the second case, there being a terminal block in the second case.

4. The combination as in claim 1, 2, or 3, at least some walls of the cases being provided with cooling ribs.

5. The combination as in claim 4, some of the ribs being on the inside, some being on the outside of the respective case.

6. The combination as in claim 4, and including power circuit elements mounted on one of the walls of the second case provided with cooling ribs.

7. The combination as in claim 3, said means for hinging the frame in the second case including pins on the terminal block.

8. The combination as in claim 3, said terminal block and a side wall of the second case defining a space for cable leading to the terminal block.

9. The combination as in claim 1, the frame being removably mounted thereto.

10. The combination as in claim 1, said door of the second case having a window.

* * * * *